United States Patent [19]

Masuhara et al.

[11] Patent Number: 5,135,685
[45] Date of Patent: * Aug. 4, 1992

[54] METHOD AND APPARATUS FOR CONTINUOUS HARDENING OF VISIBLE LIGHT-CURING RESINS

[75] Inventors: Eiichi Masuhara, Tokyo; Shigeo Komiya, Urawa; Takeyuki Sawamoto, Tokyo; Shusuke Kimura, Yono; Koji Ozeki, Yono; Kensuke Nakajima, Yono, Kiyomi Sanbonmatsu, Yono; Noboru Nishiyama, Yono, all of Japan

[73] Assignee: Japan Institute of Advanced Dentistry, Tokyo, Japan

[ * ] Notice: The portion of the term of this patent subsequent to Aug. 4, 2009 has been disclaimed.

[21] Appl. No.: 459,159

[22] Filed: Dec. 29, 1989

[30] Foreign Application Priority Data

Sep. 1, 1989 [JP] Japan .................. 1-226970

[51] Int. Cl.⁵ .............................................. B29C 35/08
[52] U.S. Cl. .................................... 264/22; 264/1.4; 264/17; 264/19; 264/40.6; 264/297.7; 425/143; 425/174.4
[58] Field of Search .................. 264/17, 18, 22, 25, 264/26, 19, 297.7, 1.4, 40.7; 425/143, 174, 174.4, 808, 150

[56] References Cited

U.S. PATENT DOCUMENTS

| | | | |
|---|---|---|---|
| 4,073,835 | 2/1978 | Otsuki et al. | 264/22 |
| 4,132,518 | 1/1979 | Rips | 425/143 |
| 4,267,133 | 5/1981 | Kohmura et al. | 264/18 |
| 4,329,135 | 5/1982 | Beck | 264/26 |
| 4,439,380 | 3/1984 | Michl et al. | 264/17 |
| 4,624,810 | 11/1986 | Sisbarro | 264/25 |
| 4,879,073 | 11/1989 | Kromrey | 425/174 |
| 4,890,997 | 1/1990 | Beins et al. | 425/174 |
| 4,913,859 | 4/1990 | Overton et al. | 264/22 |

FOREIGN PATENT DOCUMENTS 3428688 2/1986 Fed. Rep. of Germany ... 425/174.4

Primary Examiner—Jeffery Thurlow
Assistant Examiner—Mathieu Vargot
Attorney, Agent, or Firm—Armstrong, Nikaido, Marmelstein, Kubovcik & Murray

[57] ABSTRACT

A method and apparatus to continuously harden articles made of visible light-curable resins, including continuously moving the articles to be hardened relative to a multiplicity of sources of visible light which are independently controllable to be able to vary the radiation to which the articles is exposed during its passage while independently controlling the temperature at which this takes place; and apparatus to accomplish this such that a large number of the objects to be irradiated passing through the hardening apparatus have the same exposure history to the visible light and to heating or cooling respectively. As the result, there is substantially no variation in the physical properties of these photopolymerized products.

13 Claims, 3 Drawing Sheets

METHOD AND APPARATUS FOR CONTINUOUS HARDENING OF VISIBLE LIGHT-CURING RESINS

BACKGROUND OF THE INVENTION

The prevent invention relates to a hardening method and an apparatus for the visible light-curing resins, and in particular to a continuously hardening method and apparatus for the visible light-curing resins by continuously hardening the objects to be irradiated consisting of visible light-curing resins while they are moved.

Conventionally, the hardening of visible light-curing resins has been performed by a hardening apparatus, comprising an exposure stage to place an object of visible light-curing resins in an enclosure and a visible light irradiation equipment to generate the visible light. It is mostly applied for the hardening of the dental materials using composite resins in the field of dentistry.

For example, the Japanese Provisional Patent Publication Sho 62-38149 describes a hardening apparatus comprising fluorescent lamps emitting the visible light with wavelength of 400-500 nm and a stand, on which the object to be irradiated is rotatably placed, and the Japanese Provisional Patent Publication Sho 62-47354 discloses a hardening apparatus having a halogen lamp as the light source of the irradiation light and a turntable to place the object to be irradiated.

These conventional hardening methods and apparatuses for the visible light-curing resins have the following advantageous features:

1) Because the irradiation light is visible light, there is no possibility to adversely affect the clothings or the skin of the users as often seen in case of ultraviolet ray or infrared ray; 2) Because the irradiation light is visible light, there is few loss of light due to scattering in the object to be irradiated as in the case of ultraviolet ray, and the irradiated object can be hardened deep into the core. Namely, the object with larger thickness can be easily hardened; 3) Because the stand to place the irradiated object is rotatable, the illuminance on the object is distributed evenly, and the entire object can be evenly hardened.

In order to further develop the above advantageous features of the hardening method and apparatus of the visible light-curing resins, the Japanese Provisional Patent Publication Hei 1-130920 discloses a method, by which a light-curable monomer and/or prepolymer is placed in a molded frame consisting partly of the object with light transmission property to produce the molded objects for optical application such as contact lenses or lenses for eyeglasses or the molded objects for electrical and mechanical applications such as compact disk, display plate, micro-screws, gears, etc.

However, when a number of objects of visible light-curing resins are to be produced by the conventional technique as described above, the following problems arise:

1) The conventional hardening apparatus for visible light-curing resins is of batch type to harden one or more objects at one time, and it is necessary to repeatedly carry and take the objects into and from the hardening apparatus and to irradiate the objects by many times. Thus, complicated procedure and much time are required for hardening.
2) Halogen lamp, xenon lamp or fluorescent lamp used as visible light source in the conventional technique have wide variations in product quality (particularly, in luminous intensity), and the variations usually range between 10-50%.

Therefore, when the halogen lamps of the same standards are used, for instance, there are the variation of 10-50% in the illuminance of the irradiation light on the object, and this leads to the wide variations in the quality of the hardened products.

Also, there is the problem of deviation in the positions of the light source in the hardening apparatus between the product batches, and the illuminance of the irradiation light on a number of objects produced in two or more batches widely differs from each other even when the batch type hardening apparatuses of the same standards are used.

3) Even when a large quantity of the hardened products are to be produced by repeatedly using the batch type hardening apparatus for visible light-curing resins based on the conventional technique, it is impossible to obtain the hardened products from the visible light-curing resins having a constant property because the thermal history differs according to each batch.

Specifically, in the batch type hardening apparatus, the atmosphere temperature in the hardening apparatus is increased from normal temperature to high temperature due to the heat generated from the light source of the irradiation light or to the heat generated by polymerization reaction of visible light-curing resins. Also, when the hardened objects are taken out, the temperature is decreased to normal temperature, and the atmosphere temperature during the irradiation of visible light changes from normal temperature to high temperature and then to normal temperature. Thus, it is difficult to have the same thermal history for each batch, and this means that the hardened products produced from the batches widely differ in their physical property (such as surface hardness, mechanical strength, etc.).

When a number of the objects are distributed to two or more batch type hardening apparatuses of the same standards, the physical property of the hardened products thus produced widely differs, and the complicated hardening procedure and much labor and time are required.

In the method and apparatus to perform the hardening of light-curing resins by irradiation light, the method and the apparatus using ultraviolet light as the irradiation light has been widely known. Also widely known are the method and the apparatus to irradiate the ultraviolet light using high pressure mercury vapor lamp or arc discharge lamp as light source and to irradiate the light by continuously moving the objects made of ultraviolet light-curing resins.

However, because ultraviolet light is used as the irradiation light in this case, it is disadvantageous because of the loss of light due to the scattering of light within the objects and to the difficulty to perform polymerization hardening to the core of the thick objects because of the ultraviolet absorption of the ultraviolet light-curing resins itself. Accordingly, when ultraviolet light is used, the thickness of light-curable monomer and/or prepolymer is limited to the ink, film, coating film, etc. having thickness of several $\mu$m to several hundreds of $\mu$m. Namely, when ultraviolet light is used as the irradiation light, the interior of the hardened objects remains unpolymerized and satisfactory bracket cannot be obtained even if the composite resin containing inorganic filler is filled in the mold with light transmission property and the orthodontic bracket is to be molded and hardened. Even when ultraviolet light-curing resins containing coloring agents are used, hardening is performed only insufficiently, and even a color plate with thickness of about 2 mm cannot be molded.

To avoid the above problems when ultraviolet light is used as the irradiation light, the illuminance may be increased to such degree that the hardening to the deep core can be accomplished, whereas the surface of the irradiated object is exposed to extremely strong ultraviolet light in such case.

As the result, the hardened products may be thermally deformed due to extreme temperature rise, or coloring or discoloring or even ignition may occur in some cases.

SUMMARY OF THE INVENTION

To solve the above problems, the present invention proposes 1) a continuous hardening method for visible light-curing resins, characterized in that the visible light from the visible light irradiation equipment disposed at a certain position is irradiated on the objects consisting of visible light-curing resins continuously in moving, and 2) a continuous hardening apparatus for visible light-curing resins, comprising a continuous moving equipment for the irradiated objects made of visible light-curing resins and a visible light irradiation equipment disposed at a certain position.

The "continuous movement" as mentioned in this invention is that the objects to be irradiated are introduced one after another to the irradiation position within the hardening apparatus and are moved out of there. Accordingly, it includes not only the smooth movement but also intermittent movement of the objects to be irradiated.

According to this invention, visible light from the visible light irradiation equipment disposed at a certain position is irradiated on the objects made of visible light-curing resins continuously in movement. Accordingly, a number of the objects coming through the hardening apparatus have the same exposure history although the illuminance normally differs at a certain point within the hardening apparatus and at another point (e.g. near the inlet or at the center of the apparatus).

As the result, there is no variation of physical property among a number of the hardened products produced by light-curing.

Because visible light is used as the irradiation light, the influence of the scattering and absorption of light within the irradiated objects are reduced to the lower level, and the photo-polymerization hardening can be accomplished to the deep core of the molded products of visible light-curing resins having thickness of 10 mm or more.

The time from the introduction of the objects into the hardening apparatus to the moving out is preferably within the range of 1 second to 24 hours, and more preferably within the range of 10 seconds to 3 hours.

The moving mechanism may include the means to move the objects continuously at all times such as belt conveyor or turntable, or the moving means to move the objects stepwise according to the stroke such as walking beam conveyor, pneumatic or hydraulic cylinder, etc. Or, pulse motor may be used, which moves the objects by numerical control.

The movement of the irradiated objects may be linear or curved movement on the same plane or upward or downward movement.

As the light sources to generate the irradiation light, the light source having main wavelength of 400–700 nm such as halogen lamp, xenon lamp, fluorescent lamp, etc. may be used.

The light source may be furnished with a reflection mirror or a diffusion plate as already known or with a heat-cut filter to provide and control the distribution of the illuminance as desired or to give the effect to reduce the temperature rise of the irradiated objects.

The illuminance of the visible light to be irradiated is preferably in the range of 100 luxes to 10,000 kiloluxes, and more preferably from 1,000 luxes to 1,000 kiloluxes.

The visible light is preferably irradiated under the controlled atmosphere temperature to the objects made of visible light-curing resins, and this can be achieved by furnishing fan, cooling water, cooler, heater and infrared generator at the desired positions in the apparatus. In addition, temperature control may be accomplished by selecting halogen lamp (high temperature range) and fluorescent lamp (low temperature range) as the light source for visible light irradiation equipment, considering the types of lamp and the desired illuminance of the irradiation light.

As the atmosphere temperature to irradiate the visible light according to the present invention, it is preferable to control the temperature within the range of 4°–95° C., and more preferably to 20°–60° C.

The visible light-curing resins suitable for the purpose of this invention include one or more mixtures of the compounds having at least one unsaturated carbon-carbon double bond in the molecule, including monofunctional (meth)acrylic acid derivative, such as methyl (meth)acrylate, ethyl(meth) acrylate, cyclohexyl(meth)acrylate, etc. or multifunctional acrylate such as ethylene-glycol-di(meth)acrylate, diethylene-glycol-di(meth)acrylate, bisphenol-A-di(meth)acrylate, etc., added with small quantity of photoinitiator activated by the visible light. "(Meth)acrylic" as mentioned in this invention means "methacrylic" and "acrylic".

Further, photo-sensitizer or reducing agent such as tertiary amine may be used when necessary.

Also, the above components may be filled with organic or inorganic fillers or added with anti-oxidant, antistatic agent, coloring agent, thermal polymerization inhibitor, etc.

DESCRIPTION OF THE PREFERRED EMBODIMENTS

In the following, the invention will be described in detail by the embodiments in connection with the drawings:

The compound having at least one unsaturated carbon-carbon double bond in the molecule of visible ray polymerization type resin used for the present invention includes: Monofunctional (meth)acrylic acid derivative such as methyl(meth)acrylate, ethyl(meth) acrylate, propyl(meth)acrylate, cyclohexyl(meth) acrylate, benzyl(meth)acrylate, (meth)acrylic acid, hydroxyethyl(- meth)acrylate, hydroxypropyl(meth) acrylate, etc. and polyfunctional (meth)acrylate such as ethyleneglycol-di(meth)acrylate, diethylene-glycol-di(meth)acrylate, triethyleneglycol-di(meth)acrylate, bisphenol-A-di(meth)acrylate, bisphenol-A-ethylene-glycol modified di(meth)acrylate, bisphenol-A-propyleneglycol modified di(meth)acrylate, bisphenol-A-glycerol modified di(meth)acrylate, trimethylol-propane-tri(meth)acrylate, etc.

As photo-initiator activated by the visible light, there are: Dicarbonyl compounds such as camphorquinone, benzil, anthraquinone, di-α-naphthyldiketon, etc. or thioxanthone derivatives such as 2-chlorothioxanthone, 2-methylthioxanthone, 2,4-dimethyl-thioxanthone, etc. As inorganic and organic fillers, there are: glass beads, silica fine powder, titanium oxide fine powder, glass fiber, whiskers, carbon fiber, various types of polymer powder, etc.

Embodiment 1

Figure 1:
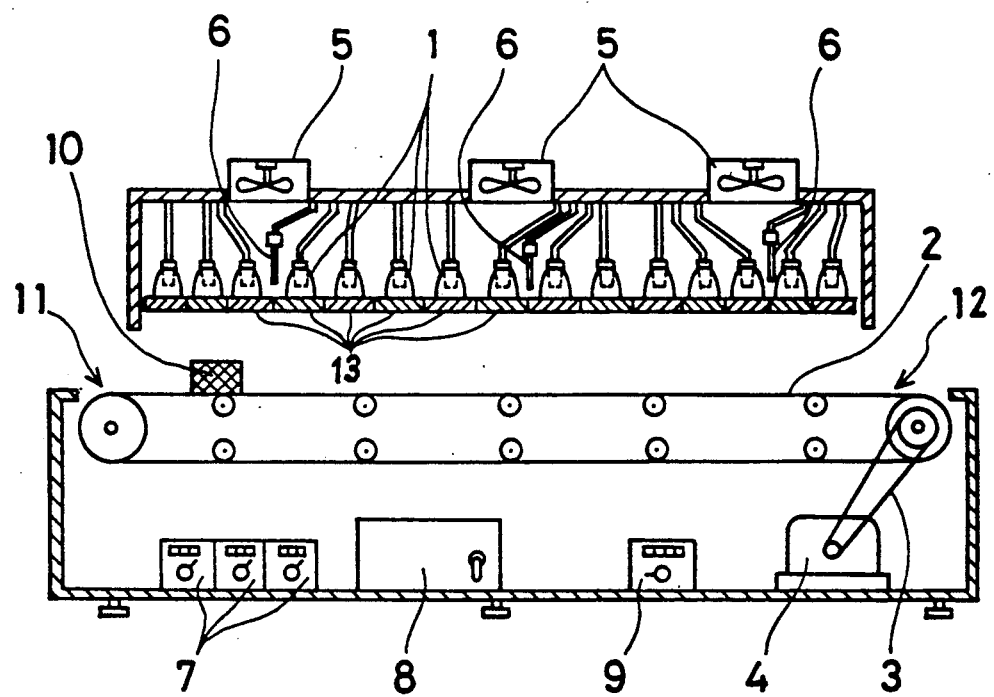
FIG. 1 is a schematical view of the Embodiment 1 according to the present invention.

FIG. 1 is a schematical view of an apparatus showing Embodiment 1 according to this invention. This apparatus is furnished with 15 halogen lamps of 150W each as the light source for the visible light irradiation equipment, and the halogen lamps 1, ... are linearly arranged above the conveyor 2 driven by the chain 3, which transmits the rotation of the motor 4.

In this apparatus, the atmosphere temperature (ambient temperature) of the irradiated objects is detected for each of three zones by 3 temperature sensors 6, and the temperature is controlled to the desired value by 3 cooling fans 5, which are stopped by 3 temperature controllers 7 for each zone.

The operating speed of the conveyor 2 in this apparatus can be arbitrarily set by the conveyor speed regulator 9.

The power for 15 halogen lamps 1 are supplied by the power source 8. In front of the halogen lamp 1, which acts as a light source for the visible light irradiation equipment, a heat cut filter 13 is furnished to eliminate heat rays, and this prevents the unnecessary temperature rise of the irradiated objects when visible light is irradiated.

Next, description will be given on the method to harden the objects consisting of visible light-curing resins by the apparatus of this invention.

In this apparatus, the object 10 consisting of visible light-curing resins is placed at the object inlet 11 of the apparatus and the conveyor 2 is driven. By the action of the conveyor 2, the object 10 is continuously moved below the halogen lamps 1, irradiating visible light under the controlled ambient temperature, and reaches soon the object outlet 12, terminating the hardening process.

In case a large number of the objects are to be hardened by this apparatus, the objects may be introduced into the apparatus from the object inlet 11 one after another according to the moving speed of the conveyor 2. As the result, the hardened objects continuously come out of the object outlet 12 after undergoing the same exposure of the visible light and the heating.

Next, description will be given on the case where orthodontic brackets are hardened and molded using the visible light-curing resins by the apparatus of this invention.

Into a light transmission type mold made of poly-4-methyl-1-pentene for the molding of bracket, the visible light-curing resins were injected, which was composed of 52 weight parts of bisphenol-A-ethyleneglycol modified dimethacrylate, 39 weight parts of methyl methacrylate, 9 weight parts of aerosol silica with hydrophobic treatment (Nippon Aerosil Co.; R-972), 0.7 weight part of camphorquinone, and 0.7 weight part of dibenzoyl peroxide.

Then, the light transmission type molds filled with visible light-curing resins were supplied one after another to the object inlet 11 and were introduced into the apparatus.

The conveyor of this apparatus is 210 cm long, and the moving speed of the conveyor 2 was 15 cm/min.

The illuminance of visible light was $140\pm30$ kiloluxes above the conveyor 2, and the atmosphere temperature in the apparatus was controlled to $45\pm2°$ C.

The objects thus irradiated were obtained one after another from the object outlet 12, and the molds were disassembled and the polymerized and hardened brackets were taken out.

The brackets were hardened to the deep core. For 30 brackets of visible light-curing resins thus obtained, the base of the bracket was cemented on the stand for the tensile test, and piano wire was attached on its wing. Thus, the tensile test of the wing was performed using a universal testing machine of Instron Co. The rupture strength of the braket wing was $3.7\pm0.5$ kgf with very small variations, showings stable property of the products. This apparatus has high productivity, producing 250 brackets per hour.

Embodiment 2

Figure 2:
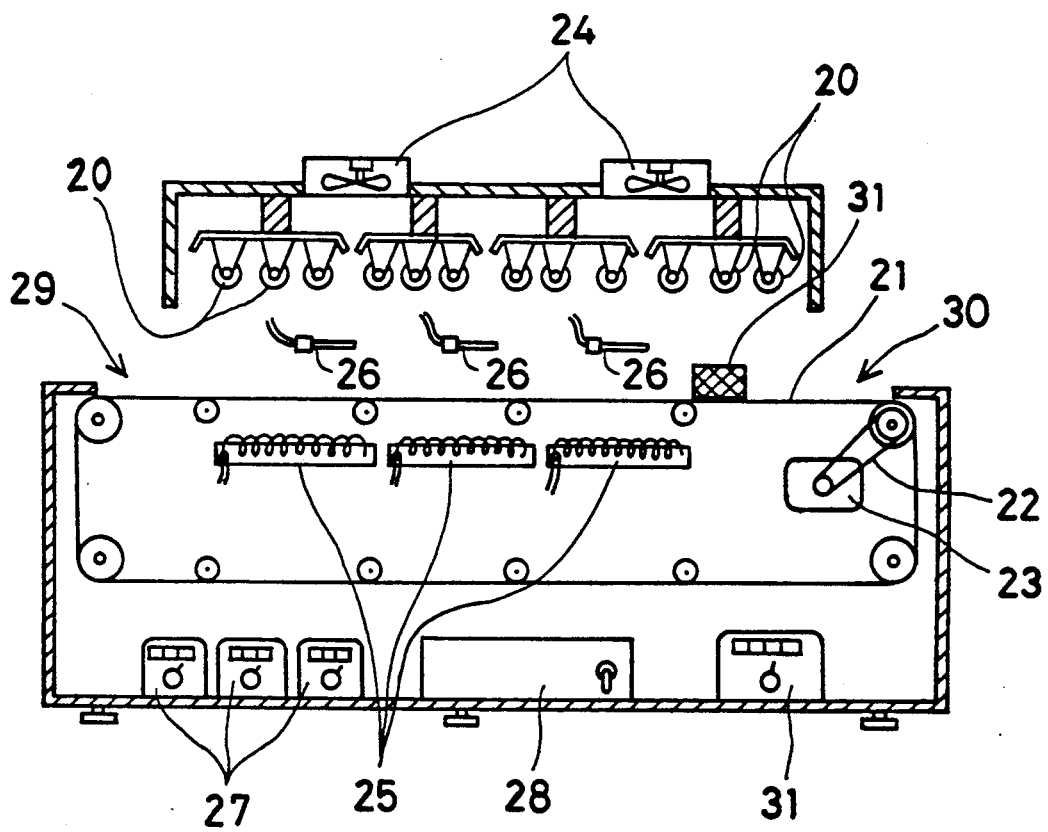
FIG. 2 is a schematical view of the Embodiment 2.

FIG. 2 is a schematical view of the Embodiment 2 according to this invention. This apparatus is furnished with 12 fluorescent lamps 20 of 20W each, in four groups of three lamps emitting the light with main wavelength of 450 nm. Similarly to the Embodiment 1, a conveyor 21 is provided, which is driven by the chain 22, transmitting the rotation of the motor 23.

In this apparatus, the atmosphere temperature is detected by the temperature sensors 26 at three points. In order to maintain the temperature set by the temperature controller 27, the heaters 25 are furnished under the conveyor 21 and the exhaust speed of the cooling fans 24 are controlled.

Because the fluorescent lamps 20 are used as the light source for the visible light irradiation equipment, it is possible to maintain the atmosphere temperature in the apparatus approximately to the room temperature.

The moving speed of the conveyor 21 of this apparatus is set by the conveyor speed regulator 31 as desired.

Next, description will be given to the case where paperweights are produced by embedding coins and using visible light-curing resins.

Into a polypropylene container with inner diameter of 50 mm and 25 mm deep, visible light-curing resins was placed to the depth of 5 mm, which was composed of 68 weight parts of bisphenol-A-glycerol modified dimethacrylate, 15 weight parts of methyl methacrylate, 7 weight parts of laurylacrylate, 10 weight parts of triethyleneglycol-dimethacrylate, 0.05 weight part of camphorquinone, 0.02 weight part of dibenzoyl peroxide, and 0.02 weight part of hydroquinone-monomethylether. The objects were introduced into the apparatus one after another from the object inlet 29, and a number of the support stands made of resin were produced, on which coins are to be placed in the subsequent process.

The conveyor 21 was 120 cm long, and the moving speed of the conveyor 21 was 30 cm/min. The illuminance of visible light was 48±5 kiloluxes above the conveyor 21, and the atmosphere temperature in the apparatus was set to 30±1° C.

Thus, a number of the containers having the resin support stands made of hardened visible light-curing resins at the bottom of the container were brought out. The brass coin with diameter of 30 mm and thickness of 1.5 mm was placed on the upper surface of the resin stand at the bottom of the container. After the visible light-curing resins were poured into the container, the containers were introduced again into the apparatus one after another.

In this case, the moving speed of the conveyor 21 was 3 cm/min. and the other conditions were the same.

The hardened irradiated objects were continuously carried out of the object inlet 30, and hard transparent paperweights made of the hardened visible light-curing resins embedded with coins were obtained.

When the surface hardness of 20 paperweights thus obtained was measured by micro-Brinnel hardness tester, the hardness was 13±1 Hb, and the variations of surface hardness were small, showing the stable finish of the products. This apparatus has high productivity, producing 50 molded products per hour.

Comparative Example 1

Figure 3:
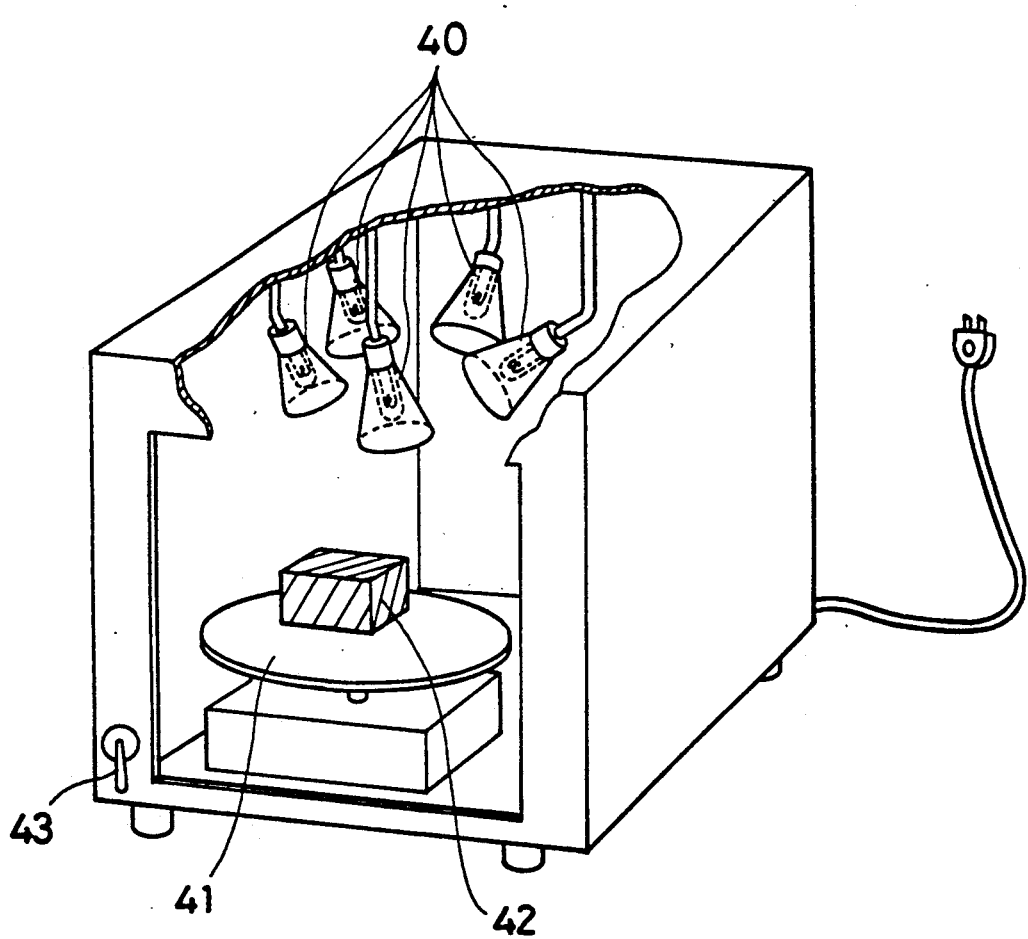
FIG. 3 is a schematical view of an equipment for comparison.

FIG. 3 is a schematical view of a comparative example.

The apparatus in this example is furnished with 5 halogen lamps 40 having the same standards as the lamps of the Embodiment 1, and the lamps are installed above the rotary turntable 41 with the irradiated objects on it as if the table 41 is surrounded by the lamps.

Using 3 apparatus of the same standards as this apparatus, orthodontic brackets made of visible light-curing resins were produced as in the case of the Embodiment 1. The visible light-curing resins having the same composition as that of the Embodiment 1 was injected into the light transmission type molds, and 5 such molds were placed on the turntable of the apparatus and the visible light was irradiated for 14 minutes for hardening. The illuminance of the visible ray of this hardening equipment on the turntable was 150±50 kiloluxes.

The brackets thus obtained had good external appearance as the brackets of the Embodiment 1, but when the tensile test of the wing was performed on 30 brackets, the rupture strength was 2.7±1.5 kgf. The mechanical strength extremely varied according to each item, and a number of defective products were found, which may not be suitable for practical application.

In this example, only 60 brackets could be produced per hour, and the productivity was lower than the Embodiment 1.

Comparative Example 2

As a comparative example, 4 units of the batch type hardening apparatus for visible light-curing resins were used to produce the paper weights by hardening the visible light-curing resins as in embodiment 2.

Each apparatus was in rectangular parallel piped shape having the dimension of 300×250×220 mm (W×D×H) and was furnished with 3 fluorescent lamps of the same stnadards as the Embodiment 2 and also with a turntable to place the objects under the fluorescent lamps. The illuminance of visible light above the table of these hardening apparatuses was 45±7 kiloluxes. The irradiation time of visible light was set to 40 minutes as in Embodiment 2.

The micro-Brinnel hardness of 20 paperweights produced by hardening the visible light-curing resins was 12±4 Hb, and the surface hardness showed extreme variations.

The apparatus of this example could produce only 10 paperweights per hour. The operation was complicated, and the productivity was low.

As described for the embodiments of this invention, a number of hardened resin molded products can be easily produced evenly by the method and the apparatus to continuously harden the visible light-curing resins according to this invention. There are not very much variations in physical property of the molded products, and it is possible to obtain the hardened products consisting of visible light-curing resins with very stable property.

Also, it is possible to produce a large quantity of the objects having thickness of 10 mm or more.

What we claim is:

1. A method to continuously harden at least one shaped article, comprising a resin containing composition which is visible sight curable, which comprises: in an enclosure, providing a multiplicity of aligned sources of visible light in which multiple groups of said sources, each group comprising less than all of them, are independently controllable; providing means to move said shaped article and said light sources continuously relative to each other; moving said article and said light sources relative to each other in relative respective alignment; continuously exposing said article to the radiation of all of the light sources along its path of relative movement; independently controlling said groups of visible light sources sufficient to continuously irradiate said article with visible light to the extent of about 100 to 1,000,000 luxes sufficient to visible light cure and harden said resin; sensing the temperature proximate to said shaped article; independently controlling the temperature of the environment about said shaped article responsive to said sensing, during said irradiation, whereby said environment temperature is controlled independent of said radiation and independent of the curing of said resin; and thus producing a cured hardened resinous article.

2. A method as claimed in claim 1 wherein a multiplicity of resinous articles are continuously cured.

3. A method as claimed in claim 1 wherein at least some of said groups of light sources comprise one light source.

4. A method as claimed in claim 1 wherein said temperature is controlled by cooling.

5. A method as claimed in claim 1 wherein said temperature is controlled by heating.

6. A method as claimed in claim 1 wherein said groups of light sources are linearly aligned, and said article moves linearly in alignment therewith.

7. An apparatus adapted to visible-light cure and harden at least one shaped article, comprising a resinous composition which is curable by exposure to visible light, which comprises: an enclosure containing a multiplicity of aligned groups of sources of visible light; means to move said shaped article relative to said light sources while maintaining the line of movement of said article aligned with said light source alignment; means to vary the emission of visible light from said groups of light sources; means to continuously irradiate said article with visible light to an extent of about 100 to 1,000,000 luxes sufficient to visible-light cure said article; sensing means to detect the temperature proximate to said shaped article; means to control the temperature of said shaped article responsive to said sensing means during said light curing thereof independent of said radiation and independent of said curing; and means for recovering a cured, hardened shaped article.

8. An apparatus as claimed in claim 7 wherein at least one of said groups of sources of light comprises a single light source.

9. An apparatus as claimed in claim 7 wherein said means to control said temperature is a heating means.

10. An apparatus as claimed in claim 7 wherein said means to control said temperature is a cooling means.

11. An apparatus as claimed in claim 7 including means to visible light cure a multiplicity of said articles in a continuous manner.

12. An apparatus as claimed in claim 7 wherein said light source groups are linearly aligned.

13. An apparatus as claimed in claim 11 including means to move said multiplicity of articles relative to spatially fixed light source groups.

* * * * *